United States Patent [19]

Fry et al.

[11] Patent Number: 5,631,152
[45] Date of Patent: May 20, 1997

[54] RAPID AND EFFICIENT REGENERATION OF TRANSGENIC PLANTS

[75] Inventors: Joyce E. Fry, St. Louis; Hua-ping Zhou, Ballwin, both of Mo.

[73] Assignee: Monsanto Company, St. Louis, Mo.

[21] Appl. No.: 329,742

[22] Filed: Oct. 26, 1994

[51] Int. Cl.$^6$ ............................ C12N 15/00; C12N 15/05
[52] U.S. Cl. .................... 435/172.3; 435/172.1; 800/205; 935/52; 935/67
[58] Field of Search ............... 800/205; 435/172.3, 435/172.1; 47/58.03, 58.05, DIG. 1; 935/52, 67

[56] References Cited

FOREIGN PATENT DOCUMENTS

| | | | |
|---|---|---|---|
| 0270355 | 3/1994 | European Pat. Off. | 435/172.3 |
| WO94/13822 | 6/1994 | WIPO | 435/172.3 |

OTHER PUBLICATIONS

Vasil (1988) Progress in the regeneration and genetic manipulation of cereal crops. Bio/technology vol. 6, pp. 397–402.
Barcelo et al., *Plant Journal*, 5: 583–592 (1994).
Becker et al., *Plant Journal*, 5: 299–307 (1994).
Chan et al., *Plant Mol. Biol.*, 22: 491–506 (1993).
Christou et al., *Bio/Technology*, 9: 957–962 (1991).
Conger et al., *Plant Cell Rep.*, 6: 345–347 (1987).
Datta et al., *Bio/Technology*, 8: 736–740 (1990).
Davey et al., *J. Exp. Botany*, 42: 1129–1169 (1991).
Dekeyser et al., *Plant Physiol.*, 90: 217–223 (1989).
Della-Cioppa et al., *Bio/Technology*, 5: 570–584 (1987).
Fromm et al., *Bio/Tech.*, 8: 833–839 (1990).
Gordon-Kamm et al., *Plant Cell*, 2: 603–618 (1990).

Kasha et al. in "Gene Manipulation in Plant Improvement II", J.P. Gustafson (ed), Plenum Press, NY, 1990, pp. 213–239.
Knutson et al., *PNAS*, 89: 2624–2628 (1992).
Murray and Thompson, *Nucleic Acid Res.*, 8: 4321–4326 (1980).
Murashige and Skoog, *Physiol. Plant*, 15: 473–497 (1962).
Nehra et al., *Plant J.*, 5: 285–297 (1994).
Poirier et al., *Science*, 256: 520–523 (1992).
Rhodes et al., *Science*, 240: 204–207 (1988).
Rhodes et al., *Bio/Tech.*, 6: 56–60 (1988).
Shillito et al, *Bio/Tech.*, 3: 1099–1103 (1985).
Shimamoto et al., *Nature*, 388: 274–276 (1989).
Somers et al., *Bio/Tech.*, 10: 1589–1594 (1992).
Vasil et al., *Bio/Telch*, 8: 429–434 (1990).
Vasil et al., *Bio/Tech.*, 9: 743–747 (1991).
Vasil et al., *Bio/Tech.*, 10: 667–674 (1992).
Vasil et al., *Bio/Tech.*, 11: 1553–1558 (1993).
Wan et al., *Plant Physiol.*, 104: 37–48 (1994).
Weeks et al., *Plant Physiol.*, 102: 1077–1084 (1993).
Zhou et al., *Plant Cell Rep.*, 12: 612–616 (1993).
Zhou and Konzak, *Crop Sci.*, 29: 817–821 (1989).
Zhou et al., *Plant Cell tissue and Organ Culture*, 30: 77–83 (1992).
Zhou and Konzak, *Genome*, 35: 957–961 (1992).
Ziauddin et al., *Plant Cell Reports*, 11: 489–493 (1992).

*Primary Examiner*—Gary Benzion
*Attorney, Agent, or Firm*—Arnold, White & Durkee

[57] ABSTRACT

A rapid transformation regeneration system is disclosed. This system takes two-three months to obtain transgenic plants. Transformation efficiencies are very high. This system also has been demonstrated with several different selecting systems and is particularly useful for transforming wheat.

12 Claims, No Drawings

RAPID AND EFFICIENT REGENERATION OF TRANSGENIC PLANTS

The present invention relates to genetically engineered plants. In particular it relates to a method for regenerating plant cells which have been transformed.

BACKGROUND

During the past decade, it has become possible to transfer genes from a wide range of organisms to crop plants by recombinant DNA technology. This advance has provided enormous opportunities to improve plant resistance to pests, diseases and herbicides, and to modify biosynthetic processes to change the quality of plant products (Knutson et al., PNAS, USA 89, 2624–2628, (1992); Piorier et al., Science, 256, 520–523, (1992); Vasil et al., Bio/Technology, 10, 667–674, (1992)). However, the availability of an efficient transformation method to introduce foreign DNA has been a substantial barrier for most monocot species, including maize, rice, oat, barley, and particularly wheat.

Two alternative transformation methods are currently used for monocot species: direct DNA transfer into isolated protoplasts and microprojectile-mediated DNA delivery (Shimamoto et al., Nature, 338, 274–276, (1989); Fromm et al., Bio/Technology, 8, 833–839, (1990)).

The protoplast methods have been widely used in rice, where DNA is delivered to the protoplasts through liposomes, PEG, and electroporation. While a large number of transgenic plants have been recovered in several laboratories (Shimamoto et al., (1989); Datta et al., Bio/Technology, 8, 736–740, (1990)), the protoplast methods require the establishment of long-term embryogenic suspension cultures. Some regenerants from protoplasts are infertile and phenotypically abnormal due to the long-term suspension culture (Davey et al., J. of Exp. Botany, 42, 1129–1169, (1991); Rhodes et al., Science, 240, 204–207, (1988)).

The microprojectile-mediated DNA delivery method may use immature embryos or immature embryo derived calli as target tissues. Transgenic plants have been recovered from the microprojectile bombardment method in maize, oat, barley and wheat (Gordon-Kamm et al., Plant Cell, 2, 603–618, (1990); Somers et al., Bio/Technology, 10, 1589–1594, (1992); Wan et al., Plant Physiol., 104, 37–48 (1994); Vasil et al. (1992)).

The microprojectile bombardment method generally takes 10 to 15 months to obtain transgenic plants (Gordon-Kamm et al., (1990); Vasil et al. (1992)). Even with the more recent improvements in transformation methods using immature embryos as target tissues, it still requires 4 to 6 months to recover transgenic plants (Weeks et al., Plant Physiol., 102, 1077–1084, (1993); Vasil et al., (1992); Vasil et. al., Bio/Technology, 11, 1153–1158 (1993); Becker et al., Plant J., 5, 299–307, (1994). Moreover, these methods suffer frequently from a loss in fertility in the recovered plants (Vasil et al., (1993); Becker et al., (1994)). Furthermore, the transformation frequency by these methods is very low, about one event from every thousand bombarded embryos. This transformation efficiency is too low for genetic studies and for commercial applications.

Thus, there is a need not only for a more rapid method of regenerating transformed plant tissue, there is also a need for a method that retains fertility in the resulting plants and produces a higher transformation efficiency.

SUMMARY OF THE INVENTION

The present invention provides a rapid and efficient transformation and regeneration system. The present invention is particularly useful with the transformation and regeneration of wheat plants. Plants regenerated from this system are phenotypically normal and fully fertile. The transgenes are transmitted to $R_1$ progeny in a Mendelian fashion.

In a preferred embodiment, the present invention provides a rapid and efficient regeneration system for monocot crop transformation using proliferated immature embryos as target tissues. The new system takes less than two months to obtain transgenic plants. Transformation frequencies by the new system are 5 to 100 times higher than the current methods used in other laboratories. This new system can be used with a variety of selectable marker systems, including selection using herbicides, such as glyphosate and bialaphos, as well as antibiotics such as kanamycin.

The present invention provides a method for regenerating a transformed monocotyledonous plant to contain foreign DNA comprising the steps of:

a) isolating regenerable tissue from the plant;

b) inserting into the regenerable tissue the foreign DNA where the foreign DNA comprises a selectable DNA sequence, where the sequence can function in a regenerable tissue as a selection device;

c) between about one day to about three weeks after step b) placing the regenerable tissue from step b) in a medium capable of producing shoots from the tissue where the medium further contains a compound used to select regenerable tissue containing the selectable DNA sequences; and d) after at least one shoot has formed from step c), transferring the shoot to a second medium capable of producing roots from the shoot.

DETAILED DESCRIPTION OF THE INVENTION

The present invention can be used with any plant species. It is particularly useful for monocot species. More particularly, it is useful in plant species which cannot remain in a callus state for long periods of time without losing the ability to regenerate. One particularly useful species in the present invention is wheat.

The present invention, when applied to wheat, has the advantage of being genotype independent. That is, it can be used with any type of wheat variety, including both winter and spring wheat. It can be used to produce transgenic wheat plants from spring cultivars, such as, for example, Bobwhite and Marshall as well as winter cultivars, such as, for example, Neeley.

The present invention is used to introduce foreign DNA into regenerable plant tissue. Any type of foreign DNA can be inserted into the plant species using the method of the present invention. Generally, "foreign DNA" can be defined to include any type of DNA which is inserted into a plant cell from outside the plant cell. Methods for inserting DNA into plant cells are generally well known, such as a bombardment using a device described in U.S. Pat. No. 5,179,022.

The type of DNA included in the foreign DNA can include DNA which already is present in the plant cell, DNA from another plant, DNA from a different organism, or a DNA generated externally, such as a DNA sequence containing an antisense message of a plant gene, or a DNA sequence encoding a synthetic version of a gene where the nucleotide sequence has been modified.

In one preferred embodiment, the foreign DNA contains a DNA sequence which can function in a regenerable plant tissue as a selection device. Such DNA can include a gene which would function in a regenerable plant tissue to produce a compound which would confer upon the plant tissue resistance to an otherwise toxic compound. These genes are well known in the art and can confer resistance to compounds such as antibiotics like kanamycin (Dekeyser et al., Plant Physiol., 90, 217–223, (1989)), and herbicides like glyphosate (Della-Cioppa et al., Bio/Technology, 5, 579–584 (1987)) and bialaphos (Vasil et al., (1992)). Other selection devices can be used within the scope of the present invention.

The first step in the present invention is to isolate regenerable tissue from a plant. Any regenerable plant tissue can be used in accordance with the present invention. Regenerable plant tissue generally refers to tissue which after insertion of foreign DNA can be regenerated into a differentiated plant. For example such tissues can include calli and/or embryoids from anthers (Zhou and Konzak, Crop Sci., 29, 817–821 (1989)), microspores (Ziauddin et al., Plant Cell Rep., 11, 489–493 (1992)), inflorescences (Barcelo et al., Plant Journal, 5, 583–592, (1994)) and leaf tissues (Conger et al., Plant Cell Reports, 6, 345–347, (1987)).

In one embodiment of the present invention, an immature embryo from a plant is used as a starting material. Immature embryos can be produced using known method described in the art. For instance, the production of wheat immature embryos is described by Weeks et al., (1993) and Vasil et al., (1993).

In another preferred embodiment of the present invention, the regenerable plant tissues are calli. The preferred calli are embryogenic calli. Embryogenic calli are produced from immature embryos. These calli can be produced by isolating and culturing immature embryos on a nutrient media with carbohydrate and plant growth regulators. In the preferred embodiment of the present invention, when producing embryogenic calli from wheat, the elimination of embryo axis as described by Nehra et al., Plant J., 5, 285–297, (1994) is not necessary.

Callus producing medium are well known in the art and any culture medium or preparation method can be used. In the preferred embodiment, where wheat calli are prepared, a wheat immature embryo is cultured for 1 day up to one month, preferably for 4 to 7 days, on a modified MS medium comprising about 40 g/l realrose and about 2 mg/l 2,4-D. In another embodiment, the 2,4 D can be replaced by a combination of 0.5 mg/l 2,4-D and 2.2 mg/l picloram. The medium is solidified by 2 g/l GELRITE or 4 g/l low melting agarose.

Once the regenerable plant tissue is isolated, the second step of the method is introducing the foreign DNA into the plant tissue. This process is also referred to herein as "transformation." Any method can be used to insert the foreign DNA into the regenerable plant tissue. Such methods include bombardment (Weeks et al., (1993); Vasil et al., (1992)), Agrobacterium transformation (Chan et al., Plant Molecular Biology, 22, 491–506, (1993)), electroporation of regenerable tissues (Shillito et. al., Bio-Technology, 3, 1099–1103, (1985)) and protoplast-facilitated gene delivery (Shimamoto et al., (1989); Datta et al., (1990)).

In a preferred embodiment, the regenerable tissue is transformed using the bombardment method. In this embodiment, it is also preferred that a callus tissue, most preferably an embryogenic callus, is used. After bombardment, this callus can be grown for a short period of time prior to regeneration or selection or, in accordance with a preferred embodiment of the invention, can immediately be subjected to both regeneration and selection conditions. With other transformation methods, this period may or may not be desirable, depending upon the selection method used.

In one embodiment of the invention, the regenerable tissue is grown for a short period after bombardment. The medium used for this growth period preferably does not contain any selection device or any medium capable of producing shoots. The use of a growth period depends upon the selection device used. Some selection devices benefit from the use of larger or older callus tissue before selection is applied. This growth period can be any period of time, but generally ranges from about 1 day to about one month. However, in the preferred embodiment of the invention, this growth period should be short, if one is used at all, and generally no more than about three weeks, preferably no more than about two weeks and most preferably no more than about one week and specifically from about 1 to about 7 days after bombardment. A growth period is not required in the present invention.

In another embodiment of the invention, the regenerable plant tissue can be subjected during this period after bombardment to a short period of selection prior to exposure of the regenerable tissue to a medium capable of producing shoots. Any selection compounds can be used during this period consistent with the selectable DNA sequence inserted into the regenerable tissue. Such compounds include paromomycin, glyphosate and bialaphos.

While this selection period prior to regeneration is not required under the claimed invention, if used, this period can range from about 1 day to about two weeks. More preferably, this period will range from about 1 to 7 days.

After transformation, the regenerable plant tissue is placed in a medium capable of producing shoots from the regenerable tissue where the medium further contains a compound used to select regenerable tissue containing the selectable DNA sequences. This is in contrast to the prior art where regenerable plant tissue is generally subjected first to an extended period of selection prior to exposure of the regenerable tissue to a medium capable of producing shoots.

The medium used in this step can be any medium which permits the formation of shoots from the regenerable tissue. In one embodiment, a shoot-producing compound is added to the medium. These shoot-producing compounds are well known in the art (Murashige and Skoog, Physiol. Plant, 15, 473–497, (1962); Kasha et al., Gene Manipulation in Plant Improvement II, 213–239, (1990)). Such compounds include weak plant growth regulators and include IAA, IBA, and BA at low concentrations (Becker et al., (1994); Vasil et al., (1992)). In another embodiment of the invention, a medium free of a plant growth regulator can be used to induce shoot formation (Weeks et al., (1993)).

In a preferred embodiment, where an embryogenic wheat calli is to be regenerated, the medium comprises a modified MS medium with 0.2 mg/l 2,4-D (Murashige and Skoog, (1962); Wan and Lemaux, (1994)).

The regenerable plant tissue is generally placed in this medium as quickly as possible in the present invention after transformation. Generally, this can range from about 1 day to about three weeks, but preferably from about 1 day to about two weeks. Most preferably the tissue is transferred to this medium from about one week to about two weeks after transformation. In most instances, the transfer will occur between about 5 and about 11 days.

The compound used to select regenerable tissue containing the selectable DNA sequences can be any of a variety of well known selection compounds, such as antibiotics and herbicides. Preferred compounds can include kanamycin (Dekeyser et al., (1989)), glyphosate (Della-Coppa et al., (1987)) and bialaphos (Vasil et al., (1992); Weeks et al., (1993)).

The availability of alternative selection agents is an important requirement for commercial application of agriculture biotechnology. The use of kanamycin has been less successful for cereal crops because of the high endogenous level of tolerance (Dekeyser et al., (1989)). Bialaphos has been widely used as a selection agent in cereal crop transformation (Weeks et al., (1993); Vasil et al., (1993); Becker et al., (1994); Nehra et al., (1994); Wan and Lemaux (1993)). However, it could potentially be a disaster to exclusively use genes encoding bialaphos resistance as a selectable marker in all transformation experiments. Other selectable markers are needed and our results demonstrate that the herein described rapid regeneration system works well with different selection agents.

After shoots have formed the shoots are transferred to a second medium capable of producing roots from said shoots. This medium can further contain a compound used to select regenerable tissue containing the selectable DNA sequences. Transfer to this medium occurs when sufficient shoots have developed, as generally known in the art. This occurs, for wheat, within 25 to 40 days after transformation.

The medium capable of producing roots can be any root-producing medium. These mediums are well known in the art (Weeks et al., (1993); Vasil et al., (1992)). One preferred root-producing medium is a modified MS medium without any plant growth regulator (Murashige and Skoog, (1962); Zhou et al., Plant Cell Tissue and Organ Culture, 30, 78–83, (1992)).

Once roots have been formed, the plants can then be transferred to soil and grown following methods known in the art to produce seeds.

One advantage of the above described transformation and regeneration method is that plants obtained from this process are generally fertile. The loss of fertility among transgenic plants using prior art methods is believed to be attributed to the long-term cultures before and after the transformation treatments rather than the act of transformation per se.

Another advantage of the present invention it that the current bombardment methods require 4 to 6 months to obtain transgenic plants (Becker et al., (1994); Vasil et al., (1992), (1993); Weeks et al., (1993)). The bombarded regenerable tissues of these prior art methods were subcultured on selection media for 2 to 3 months or longer to allow callus proliferation. By reducing the time of the callus proliferation culture, the rapid regeneration method described herein requires less than 2 months to obtain transgenic plants.

Use of the present method also caused transformed tissues to regenerate much faster. The regenerants were also more vigorous and healthier both in culture and in soil.

The rapid regeneration system described herein also usually produces uniform, non-chimeric transformants. With the rapid regeneration method, embryogenic callus sectors are usually small at the stage of regeneration. Therefore, only a single shoot is regenerated from each callus sector. Histochemical analysis for stable GUS activity showed that leaf segments from different parts of the transgenic plants were generally uniform in GUS expression. Progeny analysis also indicates that most of the transgenic plants segregated at 3:1 ratios between tolerant and sensitive plants as a single dominant gene.

The following examples describe specific embodiments of the invention. Media used are described in Table 9. The examples are provided to better elucidate the practice of the present invention and should not be interpreted in any way to limit the scope of the present invention. Those skilled in the art will recognize that various modifications, additions, etc. can be made to the methods described herein while not departing from the spirit and scope of the present invention.

EXAMPLE 1: Transformation Using CP4 and GOX As Selectable Markers

1. Immature embryo culture A spring wheat *Triticum aestivum* cv. Bobwhite was used throughout this study. Stock plants were grown in an environmentally controlled growth chamber with 16-h photoperiod at 800 µmol $m^{-2}s^{-1}$ provided by high-intensity discharge (HID) Sylvania lights (GTE Products Corp., Manchester, N.H. 03103). The day/night temperatures were 18°/16° C. Immature caryopses were collected from the plants 14-d after anthesis. Immature embryos ("IE") were dissected and cultured on a modified MS medium (Murashige and Skoog salts, Gibco BRL) supplemented with 40 g/l maltose, 0.5 mg/l 2,4-D, and 2.2 mg/l picloram (CM4). The immature embryos were cultured at 26° C. in the dark.

2. DNA delivery Five days after the initiation of culture, immature embryos were transferred to an osmoticum treatment medium 4-h prior to bombardment. The osmoticum medium was the same CM4 with 0.35M mannitol. Thirty to 40 embryos were placed in the center of each plate, and the embryos were bombarded with a mixture of pMON19305 and pMON19328 at an 1:1 ratio. pMON19305 contains the uidA gene whereas pMON19328 carries the glyphosate-tolerant CP4 and GOX genes. CP4 is a bacterial 5-enolpyruvylshikimate-3-phosphate synthase (EPSPS) gene which expresses an enzyme highly resistant to glyphosate. The glyphosate oxidoreductase (GOX) is a bacterial gene which degrades glyphosate into aminomethyl phosphortic acid. All genes were driven by the maize ubiquitin Ubi1 promoter (Christensen et al., (1992)). Each plate was bombarded twice with a PDS 1000 powder gun. High levels of transient GUS expression were observed for every bombardment in every experiment, indicating that the DNA delivery method was very efficient.

3. Regeneration of glyphosate-tolerant plants After a 16-h post-bombardment treatment on the 0.35M mannitol medium, the bombarded embryos were transferred to the CM4 medium (Table 1) for a 1-week delay of selection. At this stage, two embryos from each bombarded plate were sampled for transient GUS assays. After a one or two-week delay, the embryos were transferred to an CM4 medium containing 4 mM glyphosate. After one to two weeks of callus proliferation culture on this selection medium, the embryos were transferred to regeneration media containing 0.1 mM glyphosate (Protocol 1). In some cases, the bombarded embryos were directly transferred to the regeneration medium one to two weeks after bombardment (Protocol 2). Shoots obtained from the regeneration media were transferred to a rooting medium containing 0.02 mM glyphosate. Tolerant plants were transferred to soil and grown in an environmentally controlled growth chamber as described. Two weeks later, the plants were sprayed with 8 oz/a ROUNDUP® (active ingredient glyphosate, Monsanto).

| Process | Timeframe |
|---|---|
| Protocol 1: The rapid transformation regeneration method for glyphosate selection - reduced callus proliferation culture. | |
| Culture IE on CM4 medium ↓ | 0-d |
| Bombard embryo callus ↓ | 5-d |
| Transfer callus to CM4 + 4 mM Gt ↓ | 12-d |
| Regenerate on MMS.2 + .1 mM Gt after 1 wk callus proliferation culture ↓ | 19-d |
| Root on MMSO + .02 mM Gt ↓ | 40-d |
| Transfer plants to soil | 60-d |
| Protocol 2: The rapid transformation regeneration method for glyphosate selection - eliminated callus proliferation culture. | |
| Culture IE on CM4 medium ↓ | 0-d |
| Bombard embryo callus ↓ | 5-d |
| Regenerate on MMS.2 + .1 mM Gt after 1 wk delay ↓ | 12-d |
| Root on MMSO + .02 mM Gt ↓ | 35-d |
| Transfer plants to soil | 60-d |

On callus proliferation media, there was no visual difference on embryogenesis between the tissues bombarded with and without plasmid DNA. However, when transferred to regeneration medium, green shoots were regenerated from the transformed embryos, whereas no shoots were recovered from controls bombarded without plasmid DNA. We were able to recover glyphosate tolerant shoots from most experiments. On average, about 1–2% bombarded embryos produced glyphosate-tolerant plants (see Table 1). Under our experimental conditions, transformation efficiency with the old method was very low. About 0.05% bombarded embryos produced glyphosate tolerant plants (Table 2). Transformation efficiency from the rapid method was 25-fold higher than that from the old method. The transformation frequency from the old method was equivalent to those of bialaphos selection previously reported by other groups (Vasil et al. 1992, 1993; Weeks et al. 1993; Nehra et al. 1994).

TABLE 1

Glyphosate-tolerant plants recovered from different selection regeneration regimes by the rapid regeneration method.

| Treatment | Expt/ Trt# | #I.E. | #events | #GUS pos. |
|---|---|---|---|---|
| 1 wk delay, direct regen. | 37-2 | 300 | 3 | 2 |
| | 42-2 | 350 | 3 | 3 |
| | 43-2 | 400 | 5 | 5 |
| 2 wk delay, direct regen. | 37-3 | 300 | 1 | 1 |
| | 42-3 | 350 | 3 | 2 |
| | 43-3 | 400 | 7 | 3 |
| 1 wk delay/1 wk callusing | 43-4 | 400 | 11 | 11 |
| 1 wk delay/2 wk callusing | 42-4 | 175 | 3 | 3 |
| Total | | 2675 | 36(1.3%) | |

Expt: experiment; Trt: treatment; I.E.: immature embryos; GUS: β-glucuronidase.

TABLE 2

A summary of glyphosate tolerant plants produced from the old and the rapid regeneration methods.

| Methods | #Expt | #I.E. | #events | Freq. | Months |
|---|---|---|---|---|---|
| Old | 14 | 13,000 | 6 | 0.05% | 4.5 |
| Rapid | 3 | 2,675 | 36 | 1.3% | 2.0 |

Expt: experiment; Trt: treatment; I.E.: immature embryos; Freq.: frequency.

4. Enzyme assay of CP4 and GOX Transformed Plants

Crude proteins were extracted from fresh leaves of transgenic plants following a BioRad method. CP4 and GOX proteins were probed by antibodies, and calculated as percentages of total proteins. The transgenic plants contained 0.007–0.160% and 0.004–0.062% GOX, which were equivalent to a previously confirmed transgenic plant (Table 3). Five transgenic plants had no CP4 expression. Glyphosate tolerance of these plants was probably conferred by the GOX gene.

TABLE 3

Stable GUS expression and percent CP4 and GOX protein contents of glyphosate tolerant plants.

| Transgenic lines | Stable GUS | % CP4 | % GOX |
|---|---|---|---|
| 42-2-02 | + | 0.079 | 0.014 |
| 42-3-01 | + | 0.017 | 0.009 |
| 42-3-02 | − | 0.009 | 0.051 |
| 42-4-01 | + | 0.160 | 0.017 |
| 42-4-02 | + | — | 0.007 |
| 42-4-03 | + | 0.106 | 0.022 |
| 43-2-01 | + | 0.079 | 0.038 |
| 43-2-02 | + | 0.037 | 0.017 |
| 43-2-03 | + | 0.017 | 0.018 |
| 43-2-05 | + | 0.028 | 0.028 |
| 43-3-01 | + | 0.030 | 0.017 |
| 43-3-02 | − | 0.007 | 0.004 |
| 43-3-03 | − | 0.008 | 0.004 |
| 43-3-04 | + | — | 0.011 |
| 43-3-05 | − | — | 0.020 |
| 43-3-06 | + | 0.007 | 0.004 |
| 43-3-07 | − | — | 0.045 |
| 43-3-08 | − | — | 0.027 |
| 43-4-01 | + | 0.070 | 0.062 |
| 43-4-02 | + | 0.022 | 0.012 |
| 43-4-03 | + | 0.019 | 0.042 |
| 43-4-04 | + | 0.151 | 0.035 |
| 43-4-05 | + | 0.034 | 0.044 |
| 43-4-06 | + | 0.076 | 0.028 |
| 43-4-11 | + | 0.016 | 0.017 |
| Bobwhite | | 0.001 | 0.001 |
| 16-5(CK+) | | 0.028 | 0.011 |

5. Progeny analysis of glyphosate-tolerant plants Immature embryos from the glyphosate-tolerant plants were isolated 20-d after anthesis and cultured on a germination medium (MMS medium without plant growth regulator) with 0.02 mM glyphosate. Germinated and non-germinated embryos were separated and recorded 10 day after the culture and the data were analyzed by $X^2$ test for 3:1 segregation (Table 4). $X^2$ test indicated that the transgene segregated at a 3:1 ratio as expected. The tolerant plants were then transplanted to soil and sprayed with 8 oz/a ROUNDUP®. Individuals germinated on the selection media were also tolerant to the spray.

TABLE 4

Germination test of embryos from glyphosate tolerant R₀ plants.

| Transgenic lines | % CP4 protein | % GOX protein | Germination test |  |  |
|---|---|---|---|---|---|
|  |  |  | Tolerant | Sensitive | 3:1 prob. |
| 93-42-2-2 | 0.079 | 0.014 | 31 | 11 | >0.9 |
| 93-43-2-1 | 0.079 | 0.038 | 27 | 26 | <0.01 |
| 93-43-2-3 | 0.017 | 0.018 | 48 | 9 | >0.1 |
| 93-43-2-5 | 0.028 | 0.028 | 33 | 17 | >0.1 |
| 93-43-4-1 | 0.070 | 0.062 | 24 | 10 | >0.1 |
| 93-43-4-2 | 0.022 | 0.012 | 6 | 32 | <0.01 |
| 93-43-4-3 | 0.019 | 0.042 | 39 | 13 | >0.9 |
| 93-43-4-4 | 0.151 | 0.035 | 9 | 29 | <0.01 |
| 93-43-4-5 | 0.034 | 0.044 | 52 | 6 | <0.01 |
| Bobwhite (control) |  |  | 0 | 45 |  |

EXAMPLE 2: Transformation Using the bar Gene As a Selectable Marker

1. Transformation and selection Transformation method for the bar gene was essentially the same as the CP4 and GOX genes. Immature embryos were bombarded with the pAHC25, which carries the bar and uidA genes. Both genes were driven by the Ubiq1 promoter. The bar gene encodes phosphinothricin acetyltransferase (PAT) that acetylates phosphinothricin, the active ingredient of the non-selective herbicide Basta® (Hoechst AG). The bombarded embryos were transferred to the MMS2 medium with 4 mg/l bialaphos one day after the bombardment (Protocol 3).

Protocol 3: The rapid regeneration system for bar gene transformation.

| Process | Timeframe |
|---|---|
| Culture IE on MMS2 medium ↓ | 0-d |
| Bombard embryo callus ↓ | 5-d |
| Transfer to MMS2 + 4 mg/l bialaphos ↓ | 6-d |
| Transfer to MMS0 + 4 mg/l bialaphos ↓ | 13-d |
| Transfer to sundae cup on the same medium ↓ | 30-d |
| Transfer plants to soil | 50-d |

2. Regeneration of bialaphos-tolerant plants Following a one to two week callus proliferation on the MMS2 medium, the embryos were transferred to an MMS0 regeneration medium with 4 mg/l bialaphos. Shoots and plants from the regeneration medium were transferred to sundae cups with the same medium for rooting. Bialaphos tolerant plants were recovered and transferred to soil within two months. From a total of 828 bombarded embryos in the three experiments, 566 embryos produced bialaphos-tolerant plants (Table 5). About 15% of the embryos produced single plant, 20% of them with 2 plants, 40% with 3 plants, and 25% with 4 or more plants. Each embryo was counted as a single transformation event regardless the number of plants recovered. One third (190 out of 566) of the transformation events were GUS positive. GUS activity often varied among individual events, from completely dark blue to blue stripes in vascular tissues or blue dots randomly scattered on the leaves.

Transformation frequency with bialaphos selection was much higher than glyphosate under our experimental conditions, and 10 to 100-fold higher than those previously reported for wheat and barley (Vasil et al. 1992, 1993; Weeks et al. 1993; Nehra et al. 1994; Wan and Lemaux 1993).

TABLE 5

Bialaphos-tolerant plants recovered by the rapid regeneration system.

| Expt-Trt#* | Time of callusing | No. of embryo | Bialaphos tolerant |  | GUS positive |  |
|---|---|---|---|---|---|---|
|  |  |  | No. | % | No. | % |
| Expt 44-3 | 2 wks | 269 | 212 | 78.8 | 63 | 29.7 |
| Expt 46-3 | 1 wk | 192 | 146 | 76.0 | 52 | 35.6 |
| Expt 46-4 | 2 wks | 187 | 119 | 63.6 | 42 | 35.3 |
| Expt 48-3 | 1 wk | 90 | 59 | 65.6 | 22 | 37.3 |
| Expt 48-4 | 2 wks | 90 | 43 | 47.8 | 17 | 39.5 |

Expt: experiment; Trt: treatment; GUS: β-glucuronidase.

3. Basta® spray A sample of 20 bialaphos-tolerant plants were transferred to soil and sprayed with 1% Basta® (200 g/l glufosinate, Hoechst AG). Control plants showed necrosis and browning 3-d after the spraying. The damaged leaves turned yellow and dried later on. Ten of the 20 bialaphos tolerant plants did not show any necrotic lessions after the spraying.

4. PAT assay The Basta® tolerant plants were analyzed for PAT activity following the method of De Block et al. (EMBO J, 6, 2513-2518, 1987). All Basta® tolerant plants were PAT positive, whereas no PAT activity was observed in Bobwhite control plants (Table 6).

5. Germination test and progeny analysis The Basta® tolerant plants grew normally and set seeds. Immature embryos from the plants were cultured on a germination medium with 2 mg/l bialaphos. Immature embryos from Bobwhite control plants could not germinate on the bialaphos selection medium, whereas embryos from the Basta® tolerant plants segregated into tolerant and sensitive ones. Two of the ten plants showed 3:1 segregation ratios as expected. Five had less than 3:1 segregation whereas the other three did not produce any tolerant embryos (Table 6). It is unknown at this stage what has caused the unexpected segregation. It could be due to the small size of samples or due to gene silence. Nevertheless, the production of bialaphos tolerant plants demonstrated that the rapid regeneration system is independent of selectable markers or any gene of interest.

TABLE 6

Germination test for bialaphos tolerant R₀ plants recovered from the rapid regeneration system.

| Transgenics | GUS | PAT | Germination test |  |  |
|---|---|---|---|---|---|
|  |  |  | Tolerant | Sensitive | 3:1 prob. |
| 44-3-01 | − | + | 0 | 30 | na |
| 44-3-02 | − | + | 28 | 8 | .5-.75 |
| 44-3-03 | + | + | 21 | 15 | <.05 |
| 44-3-06 | + | + | 18 | 8 | .25-.50 |
| 44-3-07 | − | + | 14 | 15 | <.01 |
| 46-3-01 | + | + | 0 | 40 | na |
| 46-3-02 | + | + | 11 | 31 | <.01 |
| 46-3-05 | + | + | 0 | 48 | na |

TABLE 6-continued

Germination test for bialaphos tolerant $R_0$ plants recovered from the rapid regeneration system.

| Transgenics | GUS | PAT | Germination test | | |
|---|---|---|---|---|---|
| | | | Tolerant | Sensitive | 3:1 prob. |
| 46-3-06 | + | + | 4 | 32 | <.01 |
| 46-3-07 | − | + | 14 | 27 | <.01 |
| Bobwhite (CK) | − | − | 0 | 40 | na |

GUS: β-glucuronidase; PAT: phosphinothricin acetyltransferase.

EXAMPLE 3: Transformation Using the nptII gene As A Selectable Marker

The rapid transformation regeneration system also was demonstrated with paromomycin selection for the nptII gene.

1. Immature embryo culture A spring wheat *Triticum aestivum* cv. Bobwhite was used throughout this study. Stock plants were grown in an environmentally controlled growth chamber with 16-h photo period at 800 μmol $m^{-2}s^{-1}$ provided by high-intensity discharge (HID) Sylvania (GTE Corp.). The day/night temperatures were 18°/16° C. Immature caryopses were collected from the plants 13 or 14-d after anthesis and cultured on a modified MS medium (Murashige and Skoog salts, Gibco BRL) supplemented with 40 g/l maltose, 0.5 mg/l 2,4-D, and 2.2 mg/l picloram (CM4). The immature embryos were cultured at 26° C. in the dark.

2. DNA delivery Five days after the initiation of culture, immature embryos were transferred to an osmoticum treatment medium 4-h prior to bombardment. The osmoticum medium was the same CM4 with 0.35M mannitol or 0.125M mannitol and 0.125M raffinose. Approximately 40 embryos were placed in the center of each plate, and the embryos were bombarded with a mixture of pMON19476 and pMON19468 at an 1:1 ratio. pMON19476 contains the enhanced 35S promoter from CaMV (Odell et al, 1985, Kay et al. 1987), the NPTII gene (Fraley et al 1983), and the NOS terminator from the nopaline synthase gene (Fraley et al. 1983). pMON19468 carries the uidA (which encodes Beta-glucuronidase (GUS) from *Escherichia coli* (Jefferson et al 1986) and the NOS terminator. Both the nptII and GUS gene were driven by the 35S promoter (Odell et al, 1985, Kay et al. 1987). Each plate was bombarded twice with a PDS 1000 powder gun as described in detail by Klein et al 1987. High levels of transient GUS expression (an average of 84 spots per embryo) were observed, indicating that the DNA delivery method was very efficient.

3. Regeneration of paromomycin-tolerant plants After a 18-h post-bombardment treatment on the 0.35M mannitol medium or a combination of 0.125M mannitol and 0.125M raffinose medium, the bombarded embryos were transferred to the CM4 medium (Table 9) for a 6 or 7 day delay of selection. At this stage, two embryos from each bombarded plate were sampled for transient GUS assays. After a 6 or 7 day delay, the embryos were transferred to a CM4 medium containing 100, 200, or 300 mg/l paromomycin for callus proliferation. Another set of embryos were transferred directly to regeneration medium containing 100 or 200 mg/l paromomycin (Protocol 4). In some cases, the bombarded embryos were directly transferred to the regeneration medium one to two weeks after bombardment (Protocol 5). Shoots obtained from the regeneration media were transferred to a rooting medium containing no selective agent (Table 9). Plants were scored for GUS by histochemical analysis. Positive plants and some negative plants (controls) were transferred to soil and grown in an environmentally controlled growth chamber as described.

4. Progeny analysis of paromomycin-tolerant plants. Immature embryos from the paromomycin-tolerant plants were isolated 20-d after anthesis and cultured on a germination medium (MMS0 medium without plant growth regulator) with 100 mg/l paromomycin. Germinated and non-germinated embryos were separated and recorded 10 day after the culture and the data was analyzed by $X^2$ test for 3:1 segregation (Table 8). $X^2$ test indicated that the transgene did not segregate at a 3:1 ratio as expected.

| Process | Timeframe |
|---|---|
| Protocol 4: The rapid regeneration system for paromomycin selection - reduced callus proliferation culture. | |
| Culture IE on CM4 medium ↓ | 0-d |
| Bombard embryo callus ↓ | 4-d |
| Transfer callus to CM4 + 100 mg/l paromomycin ↓ | 9-d |
| Regenerate on MMS ZR/NAA medium after 1,2, or 3 wks callus proliferation culture ↓ | 16-d |
| Root on MMS0 ↓ | 37-d |
| Transfer plants to soil | 72-d |
| Protocol 5: The rapid regeneration system for paromomycin selection - eliminated callus proliferation culture. | |
| Culture IE on CM4 medium ↓ | 0-d |
| Bombard embryo callus ↓ | 4-d |
| Regenerate on MMSZR/IAA medium after 5 day delay ↓ | 9-d |
| Root on MMS0 ↓ | 37-d |
| Transfer plants to soil | 72-d |

On callus proliferation media, some of the callus turned white and stopped proliferating while some parts of the callus remained yellow and proliferated. Both the yellow and white callus tissues appeared compact and embryogenic. The tissues bombarded without plasmid DNA did not proliferate and bleached. When transferred to regeneration medium, green shoots were regenerated from the transformed embryos, whereas no shoots were recovered from controls bombarded without plasmid DNA. We were able to recover paromomycin tolerant shoots from all experiments. On average, about 0.3–4% bombarded embryos produced GUS positive paromomycin-tolerant plants (Table 7). The protocol 4 produced 2 and 4% GUS positive plants while the protocol 5 produced 0.3 to 1% GUS positive plants. Both protocols produced higher transformation frequencies than those of bialaphos selection previously reported by other groups (Vasil et al. 1992, 1993; Weeks et al. 1993).

TABLE 7

Paromomycin selected plants recovered from different selection regeneration regimes by the rapid regeneration method.

| Treatment | | | | | | |
|---|---|---|---|---|---|---|
| Delay Before Selection | Time on Callusing | Paro Conc mg/l | Expt/Trt# | #IE | #Plants | #gus+ |
| 7d | 3 week | 100 | 88-02 | 400 | 30 | 4 |
| 7d | 3 week | 200 | 88-03 | 400 | 37 | 3 |
| 7d | 3 week | 300 | 88-04 | 369 | 35 | 2 |
| 5d | 0 | 100 | 91-01 | 162 | 52 | 6 |
| 5d | 0 | 200 | 91-02 | 161 | 38 | 3 |
| 5d | 1 week | 100 | 91-05 | 365 | 29 | 1 |
| 5d | 2 week | 100 | 91-07 | 364 | 23 | 4 |
| 5d | 3 week | 100 | 91-09 | 364 | 21 | 4 |
| Total | | | | 2585 | 265 | 27 |

TABLE 8

Paromomycin germination assay on $R_1$ progeny from plants transformed with the nptII gene.

| Transgenic lines* | Scorable Marker | Germination assay | | |
|---|---|---|---|---|
| | | #Tolerant | #Sensitive | 3:1 prob |
| 88-04-01-01 | Gus(+) | 30 | 50 | <0.01 |
| 88-04-02-01 | Gus(−) | 26 | 54 | <0.01 |
| 88-24-06-02 | Gus(+) | 36 | 44 | <0.01 |
| 88-14-04-02 | Anthro(+) | 37 | 43 | <0.01 |
| 88-35-01-01 | Anthro(+) | 18 | 14 | <0.01 |
| Control BW | none | 0 | 80 | NA |

*Plants transformed with either:
pMON19476 (E35S/HSP70/NPTII) + pMON19468 (E35S/HSP70/GUS) or pMON19476 (E35S/HSP70/NPTII) + BC17 anthocyanin

TABLE 9

Tissue Culture Media used for wheat callus development, and regeneration of plant cells.

| Medium Name | MS* | Carbohydrate per liter | pH | Additional Components mg/l |
|---|---|---|---|---|
| CM4 | + | 40 g maltose | 5.8 | 500 glutamine<br>750 MgCl<br>100 casein hydrolysate<br>0.5 2,4-D<br>2.2 picloram |
| MMSZR/IAA | + | 40 g maltose | 5.8 | 500 glutamine<br>750 MgCl<br>100 casein hydrolysate<br>5 Zeatin riboside<br>1 IAA |
| MMS2 | + | 40 g maltose | 5.8 | 2 2,4-D |
| MMS.2 | + | 40 g maltose | 5.8 | 0.2 2,4-D |
| MMS0 | + | 20 g sucrose or 40 g maltose | 5.8 | |

*Basal MS medium described in (Zhou et al. 1993)
2 g/l gelrite used for all media except paromomycin selection medium which contains 4 g/l agarose.

The above examples demonstrate the transformation method using three selection devices. One skilled in the art would recognize that this method can be applied to many selection systems and that the invention is not limited to these examples but only limited by the attached claims.

We claim:

1. A method for regenerating a fertile transformed wheat plant to contain foreign DNA comprising the steps of:
   (a) producing regenerable tissue from said plant to be transformed;
   (b) transforming said regenerable tissue with said foreign DNA where said foreign DNA comprises a selectable DNA sequence, where said sequence functions in a regenerable tissue as a selection device;
   (c) between about one day to about 21 days after step b) placing said regenerable tissue from step b) in a medium capable of producing shoots from said tissue wherein said medium further contains a compound used to select regenerable tissue containing said selectable DNA sequence to allow identification or selection of the transformed regenerated tissue;
   (e) after at least one shoot has formed from the selected tissue of step c), transferring said shoot to a second medium capable of producing roots from said shoot to produce a plantlet; and,
   (e) growing said plantlet into a fertile, transgenic wheat plant wherein the foreign DNA is transmitted to progeny plants in mendelian fashion.

2. The method of claim 1 where said regenerable tissue is moved to the medium of step c) between from about one day to about two weeks after step b).

3. The method of claim 1 where said regenerable tissue is moved to the medium of step c) between from about five days to about eleven days after step b).

4. The method of claim 1 where said selectable DNA sequence expresses an enzyme which will confer resistance to at least one of the group consisting of kanamycin and paromomycin to said plant cell.

5. The method of claim 1 where said selectable DNA sequence expresses an enzyme which will confer resistance to glyphosate to said plant cell.

6. The method of claim 1 where said selectable DNA sequence expresses an enzyme which will confer resistance to bialaphos to said plant cell.

7. A method for regenerating a fertile transformed wheat plant to contain foreign DNA comprising the steps of:
   (a) producing embryogenic calli from said plant to be transformed;
   (b) transforming said calli with said foreign DNA where said foreign DNA comprises a selectable DNA sequence, where said sequence functions in a regenerable tissue as a selection device;
   (c) between about one day to about 21 days after step b) placing said regenerable tissue from step b) in a medium capable of producing shoots from said tissue where said medium further contains a compound used to select the transformed regenerable tissue containing said selectable DNA sequences to allow identification or selection of the transformed regenerated tissue;
   (d) after at least one shoot has formed from the selected tissue of step c), transferring said shoot to a second medium capable of producing roots from said shoot to produce a plantlet; and,
   (e) growing said plantlet into a fertile transgenic wheat plant wherein the foreign DNA is transmitted to progeny plants in mendelian fashion.

8. The method of claim 7 where said regenerable tissue is moved to the medium of step c) between from about one day to about two weeks after step b).

9. The method of claim 7 where said regenerable tissue is moved to the medium of step c) between from about five days to about eleven days after step b).

10. The method of claim 7 where said selectable DNA sequence expresses an enzyme which will confer resistance to at least one of the group consisting of kanamycin and paromomycin to said plant cell.

11. The method of claim 7 where said selectable DNA sequence expresses an enzyme which will confer resistance to glyphosate to said plant cell.

12. The method of claim 7 where said selectable DNA sequence expresses an enzyme which will confer resistance to bialaphos to said plant cell.

* * * * *